United States Patent [19]

Small et al.

[11] 4,414,842
[45] Nov. 15, 1983

[54] ION EXCHANGE CHROMATOGRAPHY WITH INDIRECT PHOTOMETRIC DETECTION

[75] Inventors: Hamish Small; Theodore E. Miller, Jr., both of Midland, Mich.

[73] Assignee: The Dow Chemical Company, Midland, Mich.

[21] Appl. No.: 364,705

[22] Filed: Apr. 2, 1982

Related U.S. Application Data

[63] Continuation of Ser. No. 153,814, May 27, 1980, abandoned.

[51] Int. Cl.³ .................................. G01N 21/00
[52] U.S. Cl. ....................................... 73/61.1 C
[58] Field of Search ............. 73/23.1, 61.1 C; 55/67, 55/197; 356/412

[56] References Cited

U.S. PATENT DOCUMENTS 3,988,919 11/1976 Talmi et al. ................. 73/23.1
4,233,030 11/1980 Twitchett et al. ............. 73/61.1 C

FOREIGN PATENT DOCUMENTS 882977 11/1961 United Kingdom ............ 73/23.1

OTHER PUBLICATIONS

A. Laurent and R. Bourdon (Ann. Pharm. France, 1978, 36 (9-10), 453-60), "Assay of Anions by Ion Exchange Chromatography," plus translation.
L. R. Snyder & J. J. Kirkland, Introduction to Modern Liquid Chromatography, Second Edition, pp. 419-421 & 563.
R. P. W. Scott et al., "Some Aspects of Liquid-Solid Vacancy Chromatography," Anal. Chemistry, vol. 44, No. 1, Jan. 1972, pp. 100-104.
B. A. Bidlingmeyer et al., "Retention Mechanism for Reversed-Phase Ion-Pair Liquid Chromatography," Journal of Chromatography, 186 (1979) pp. 419-434.

Primary Examiner—Jerry W. Myracle
Attorney, Agent, or Firm—Burke M. Halldorson

[57] ABSTRACT

An improved technique for the measurement of ions in solution where the ions of interest are chromatographically displaced from an ion exchange column by an eluting ion which is or is made light-absorbing, and where the eluted sample ions, which are transparent (at the monitored wavelength), are detected and quantified from the decrements they cause in effluent absorbance as revealed by photometric monitoring.

20 Claims, 16 Drawing Figures

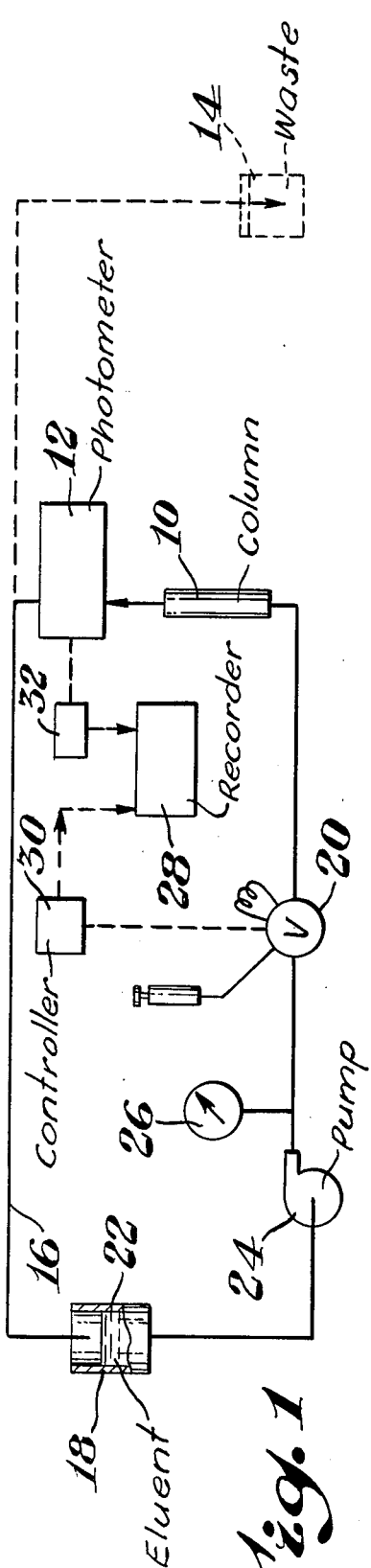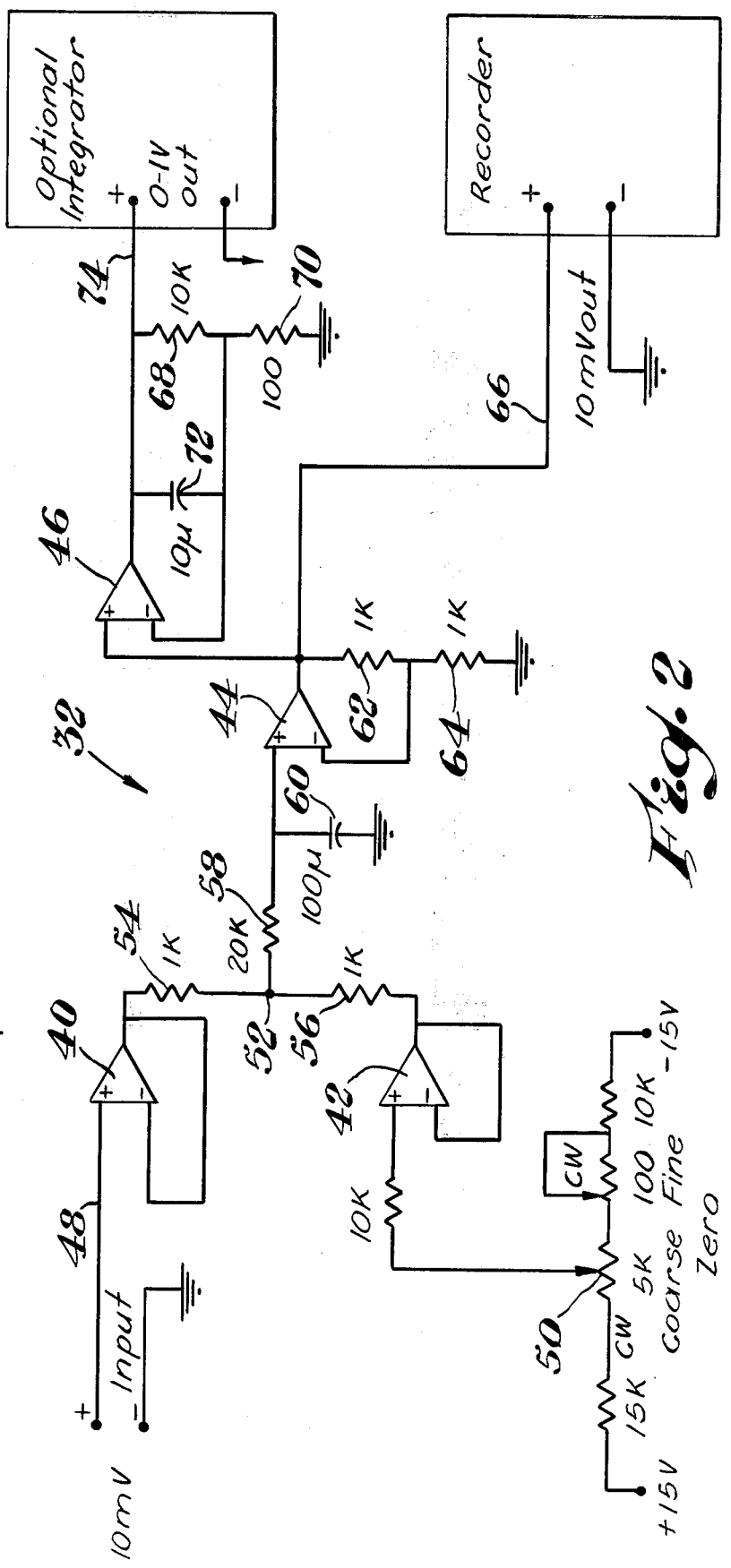

Ion exchanger solution interface

Ion exchanger solution interface

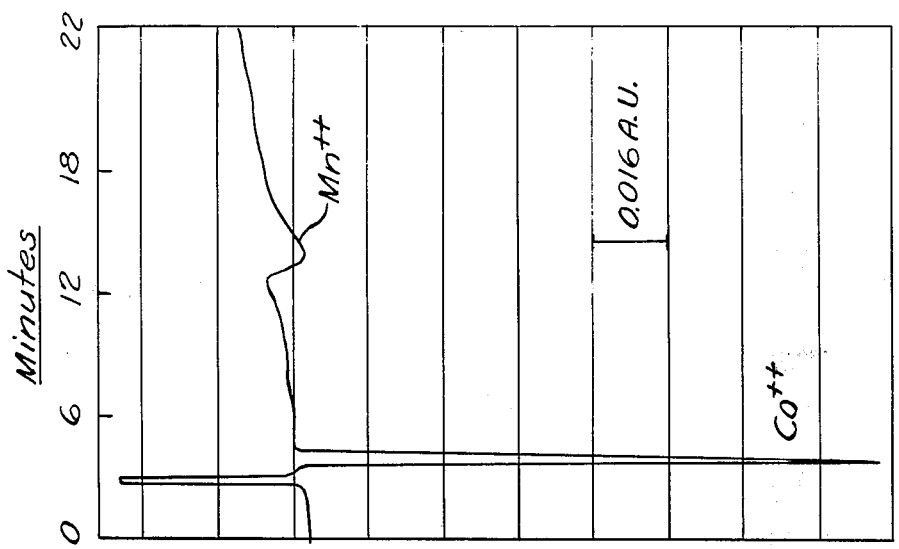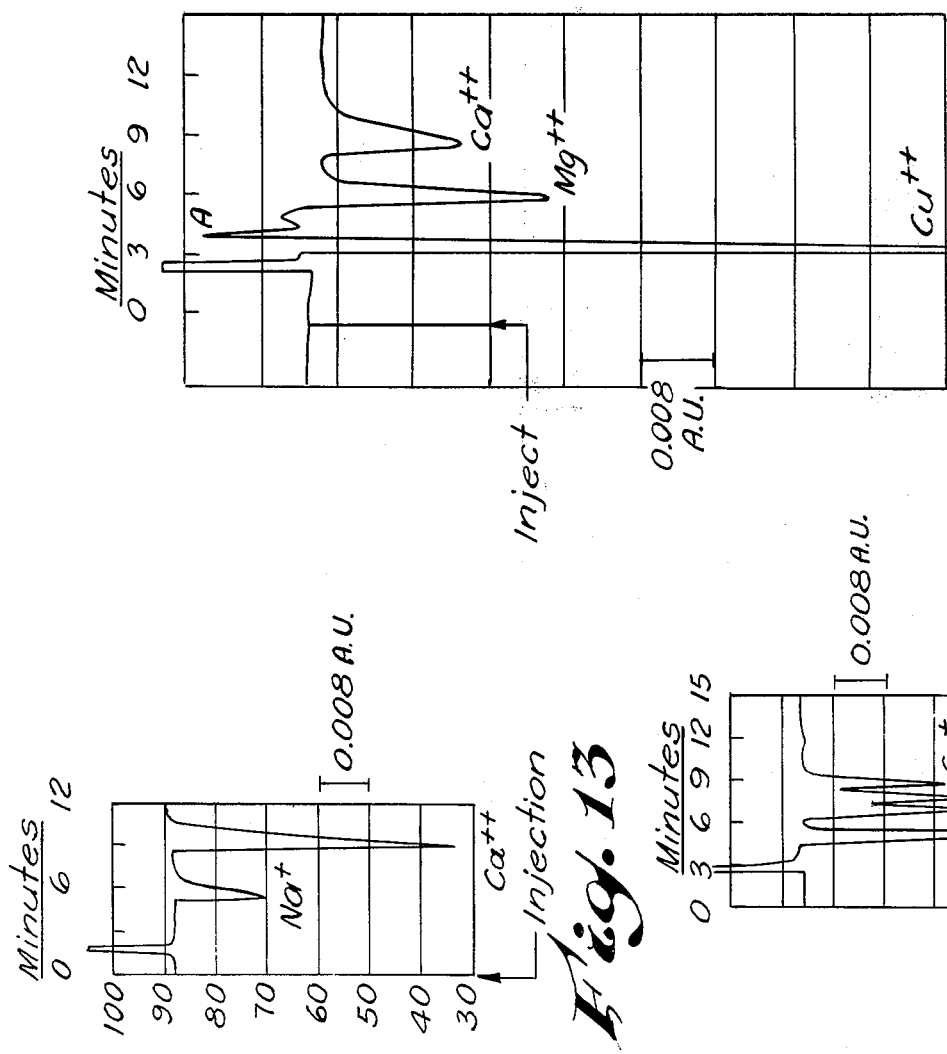

ION EXCHANGE CHROMATOGRAPHY WITH INDIRECT PHOTOMETRIC DETECTION

CROSS REFERENCE TO RELATED APPLICATION

This is a continuation of application Ser. No. 153,814, filed May 27, 1980 now abandoned.

FIELD OF THE INVENTION

The invention relates to the field of ion exchange chromatography and particularly to an improved detection scheme for use therein.

BACKGROUND OF THE INVENTION

The solution of ion analysis problems by liquid chromatography is often complicated by limitations in the capability to detect the eluted sample ions in the column effluent. An example is the problem of analyzing the many inorganic and organic ions that are non-light-absorbing. Whereas the seperation of such "transparent" ions may be conveniently effected on ion exchange resin columns, their detection and measurement by conventional photometric means is ineffective since they are optically indistinguishable from the transparent eluents commonly prescribed by the art. Hence, current and conventional practice teaches that photometers are useful only where the ions to be determined either contain chromophores or can generate chromophores through post-column reactions with appropriate reagents.

A second field of background art of interest to the invention is Ion Chromatography (IC). Ion Chromatography comprises a two column arrangement followed by a conductance detector. The first column serves to separate the ions of interest while the second column, "the suppressor", serves to lower the conductance of the eluent while not significantly affecting the conductance of the eluted sample species. The suppressor column in IC disadvantageously becomes exhausted in the course of normal usage and must be periodically regenerated or replaced—usually regenerated. Whereas the regeneration step has been automated in commercial instruments so that it is less obtrusive, it would be desirable to develop sensitive single column (suppressorless) methods for the many ions that lack chromophores for the following reasons:

(1) Reduced complexity of the instrumentation and in its operation. This is a very important factor in the process control area where the demands for unattended and relatively maintenance-free operation are most essential;

(2) Faster analysis times due to void space elimination, and less loss of resolution since the suppressor column contributes to peak broadening;

(3) Less alteration in calibration with usage. In Ion Chromatography, such changes can arise for ions whose elution behavior depends on the degree of exhaustion of the suppressor;

(4) Elimination of detrimental suppressor column side reactions, with resulting broader sample species applications; and (5) Eluent recycle capability and elimination of suppressor column regenerant.

There are other problem areas which the invention addresses. Of particular importance is the ability to determine ions by flow analysis for which past IC and photometric methods show relatively poor sensitivity. Carbonate determination is an example that is demonstrated specifically herein, and for which both IC and photometric methods are generally not ideally suited, or are unsuited for such analysis.

Another significant improvement is achieved in the area of calibration procedures. Most IC methods, as well as most methods of analysis, generally rely on a calibration procedure wherein the user establishes experimentally the relationship between peak height or peak area response and the amount of sample species injected. Each species has a response factor which is characteristic for that species and usually different from that of other species. This requires that response factors be determined for all species of interest. In contrast, in practicing the invention, it has been discovered that a number of ions will have a common response factor. This obviously and beneficially simplifies instrument operation.

THE INVENTION

The invention relates to an improved method for the flow analysis of photometrically differentiable sample and non-sample ions in a solution of photometrically monitorable liquid effluent wherein, generally, sample which is in or placed in solution is contacted with a flow-through ion exchange medium and anion or alternatively cation sample ions are exchanged at the active ion exchange sites thereof, and eluted through said ion exchange medium using a liquid eluent which contains displacing ions which displace sample ions from the ion exchange medium, eventually causing displaced sample ions to appear in the effluent of the ion exchange medium, the improvement which comprises using eluent containing light-absorbing displacing ions which are or are made detectably light-absorbing in said effluent, photometrically monitoring said effluent using light which is detectably absorbed by said light-absorbing displacing ions and which photometrically distinguishes transient sample ions sufficiently to produce an effluent absorbance response proportional to the variable concentration of the monitored light-absorbing displacing ions in the effluent, and indirectly determining the concentration of displaced sample ions of interest eluting off the ion exchange medium based on the decrements caused by same in the effluent absorbance response as detected by the photometric monitoring step.

In samples of mixed cation or anion species, where data is desired respecting the concentration of individual species, the ion exchange medium is selected to produce a chromatographic separation of cation or anion species, whichever is of interest, using displacing ions which differentially displace sample ions from the separating medium, causing the displaced ions to appear chromatographically resolved in the effluent of the separated medium and in a form whereby all or selected ion species of interest may be individually quantified indirectly according to the inventive practice.

A basic feature of the invention is in the use of light (usually U.V.) absorbing eluents which essentially include light-absorbing ions, i.e., said displacing ions, of the same charge (but not necessarily same valence) as the ions to be separated.

These light-absorbing displacing ions have a dual role of:

(1) selectively displacing the sample ions from the chromatographic column or ion exchange medium, and (2) revealing the sample ions in the effluent.

This dual functionality is recognized by the term "monitoring/displacing", and, in this respect, departs from characteristic eluents used in the past which by the logic of the prior techniques contemplate the displacing function, but not the monitoring function. The monitoring function takes unique advantage of the fact that the concentration of light-absorbing displacing ions in the ion exchange effluent varies inversely with the concentration of displaced sample ions eluting from the ion exchange medium and that this relationship or phenomenon may be applied through effluent absorbance monitoring to determine quite accurately, in a very convenient and in an indirect fashion, the concentration of displaced sample ions of interest.

The monitoring/displacing function may be obtained by way of either (a) the selection of critical displacing ions inherently possessing the proper dual functionality, or alternatively (b) ions made to possess that functionality by a conversion step during the analytical experiment, e.g., such as by use of a post-column reaction effective to convert displacing ions in the effluent to a photometrically "visible" species.

Specifically, the invention envisions the new concept embodying the selection of critical light-absorbing displacing ions, and the preparation of eluent solutions possessing a sufficient quantity of such critical ions, that an effective chromatographic displacement of the sample ions is achieved within practical and operable time limits (sometimes with the assist a major or minor amount of non-light-absorbing displacing ions optionally added to prepare optimum forms of eluent respecting specific separations); and in addition, wherein such critical ions are present sufficiently to produce detectable light absorbance in the ion exchange effluent. Since the concentration of the light-absorbing displacing ions in the ion exchange effluent varies inversely to the concentration of displaced sample ions, the appearance of displaced sample ions in the effluent is revealed by fluctuations in the effluent absorbance. These fluctuations are most generally in the form of decrements or dips or troughs appearing in the absorbance base line, at the intervals expected for the consecutive elution of the sample ion species. The dips or troughs reveal that the concentration of the light-absorbing displacing ions have given way to an increase in displaced sample ions which appear in transient fashion in the effluent corresponding to their respective elution times, producing a temporary "void" of light-absorbing displacing ions. The extent of the void (or the reduction in the concentration of the monitored eluent ions) indirectly reveals the concentration of displaced sample ions causing the "void". Whether the sample ions are greater or lesser light absorbers than the displacing ions, determines generally whether a "dip" or "peak" is registered in the absorbance response. Since strong light-absorbing sample ions may be determined quite easily by conventional photometric detection, the invention has its greatest application in the quantitative analysis of heretofore difficult "transparent" sample ion species which produce the mentioned characteristic dip in the effluent absorbance as detected by photometric monitoring.

Where a post-column reaction is employed, the principle is unchanged, except the invention envisions that the photometric detectability of the displacing ions is a feature either achieved, or enhanced, by a conversion step occurring most often in the effluent stream between the separating medium and the photometric detector. In photometric analysis, it has been known to use such reactions to produce detectable or visible sample ions. The technique as used here, however, is substantially different in concept. Thus, it is necessarily recognized that as a major and critical difference, the sample ions are beneficially unaffected in order to retain optimum transparent or "non-visible" characteristics. In contrast, the displacing ion form is modified to take on or to enhance its light absorbance properties at the monitored wavelength(s) or wavelength band, whereby a depletion or reduction of such displacing ions in the effluent can be monitored with good efficiency. Hence, the "transparency" of the sample ions is critical to the invention, and departs substantially from the photometric monitoring techniques and schemes proposed in the area of prior photometric detection methods having the opposite purpose of making sample ions of interest visible.

The separating medium or stationary phase used in the analytical methods and apparatus of the invention is an ion-exchange material or separating medium of any type effective, broadly or narrowly, in separating ionic species in combination with eluents containing displacing ions. This area of the prior art is extremely well developed, and may be broadly called upon to produce a range of materials useful in conjunction with the invention. The materials may be either in the form of "packings" (the current most preferred form), or may be of such other form as can be usefully applied to achieve sample ion separations by the principle of ion-exchange elution chromatography in the broad sense. Exemplary of the latter is the use of hollow fiber membranes or capillary tubes to perform separations with the aid of eluents of the basic type specified herein (i.e., eluents containing displacing ions).

The medium is also sometimes referred to herein more broadly as an "ion exchange medium" in connection with samples or types of analysis which do not require a chromatographic resolution, e.g., certain forms of total ion analysis. It may nevertheless comprise beneficially the same materials as where a resolution of species is required or practiced.

The liquid eluent is normally prepared using as the solvent deionized water. Other highly polar solvents known for ion exchange chromatography such as the lower alcohols of 1–4 carbon atoms, may be admixed with water or used solely to dissolve the electrolyte component(s). It is necessary, of course, to select eluent solvents, from those known in the art, which permit the light-absorbing displacing ion concentration of the eluent (in the effluent of the ion exchange medium) to be photometrically determined.

The photometric detector is chosen according to the wavelength(s) or wavelength band being monitored, and is thus selected depending on the light absorbance characteristics of the displacing ions. More specifically, visible or U.V. photometric detectors of the various types known in the art, for use with liquid chromatography, can be suitably applied to applications involving the invention.

It is not absolutely essential that the sample ions be transparent at all wavelengths. It is required only that the same be nonabsorbing at the select wavelength(s) or wavelength band monitored; or alternatively, of characteristically different absorbance, vis-a-vis the displacing or monitored ions, at the monitored wavelengths(s), such that presence of sample ions, reducing the concentration of the displacing ions in the effluent, produces a fluctuation in the absorbance base line which is proportional to the reduction of monitored displacing ions. The fluctuation must, of course, be sufficient to quantify, at the desired sensitivity level, the concentration of sample ions of interest, based on the departure from base line absorbance levels.

THE DRAWING

Yet further objectives, aspects, and advantages of the invention will, in part, be pointed out and, in part, apparent from the following detailed description considered together with the accompanying Drawing wherein:

FIG. 1 is an elevational view of apparatus for performing ion exchange chromatography with indirect photometric detection in accordance with the principles and teachings of the present invention;

FIG. 2 is a circuit diagram showing the electronic interface between the FIG. 1 apparatus and a visual reader such as a strip chart recorder and/or integrator;

FIGS. 7 through 16 are illustrations of various chromatograms together with a calibration graph, developed using the method of the invention, and are particularly associated with the teaching Examples 1–11, below.

DETAILED DESCRIPTION

Figure 3:
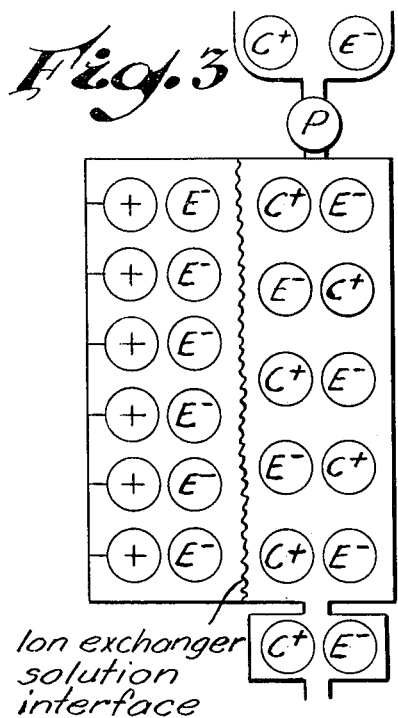
FIGS. 3 and 4 are exaggerated diagrammatic views adapted for illustration of the principle of the separation and detection scheme practiced by the invention.

Referring to FIG. 1, there is shown a typical schematic of an ion-exchange chromatography instrument or apparatus which is desirably used in practicing the invention, and which comprises a chromatographic separating means comprising an ion exchange liquid chromatography column 10 which is packed with an ion-exchange separating medium. Most media in the art are in the form of pellicular or micro-particulate ion-exchange resins. The invention may employ, however, any form of ion-exchange separating medium useful in separating cations or anions, such as capillary tubes, or such other separating medium as is found or known to be useful to perform ion separations by eluting a sample therethrough using an eluent which contains displacing ions.

Column 10 is followed by a photometric detector 12, preferably a flow-through U.V. photometer with micro-volume cell design for HPLC applications. For visible light, the invention preferably employs the same photometer modified to incorporate a tungsten lamp light source. The analytical stream is ultimately dispelled from the photometer to waste vessel 14 or to recycle. The preferred application employs a recycle or return line 16, whereby the spent eluent/sample is returned to a reservoir 18 containing eluent or mobile phase. The return to the reservoir of the spent eluent is considered a unique feature of the invention permitted by the fact that the sample species in the spent eluent is insignificant for subsequent analyses.

Sample may be placed in column 10 in most any suitable manner but preferably, by means of a syringe, is added to the system at a sample injection valve 20. The sample injected at valve 20 is swept through the apparatus by a solution containing light-absorbing ions, i.e., eluent solution 22 drawn from eluent reservoir 18 by a chromatographic pump 24, monitored by a pressure gauge 26, and is then passed through the sample injection valve 20 to column 10. Likewise, the eluent solution may be added to column 10 manually as by pouring the solution from a vessel into an open column, but is preferably added in a continuous stream to obtain better uniformity and reproducibility of results. The solution leaving column 10 with the ionic species resolved is conveyed by a liquid conduit to the photometric detector.

In the photometric detector, the presence of light-absorbing displacing ions in the effluent produces an electrical signal proportional to the amount of such ions and which is directed from the detector ultimately to a visual recorder such as a strip chart recorder 28, which continually visually reproduces the detector signal. The decrements (or peaks) observed in the base line absorbance are ultimately related to sample ion species, to produce sample species concentration data as is described more fully below.

Desirable further features included in the apparatus of the invention include a sample injection valve controller 30, which automates the operation of the injection valve, and which is also used to superimpose a transient signal on the detector output to recorder 28 to mark the strip chart with a spike to indicate the injection event.

Also a further advantageous feature of the instrument, although not necessary for all applications, is an electronic interface module 32 which is adapted to: (1) provide additional base line biasing voltage to off-set the elevated detector base line that exists because of the use of absorbing displacing ions, and (2) provide impedance buffering to interface multiple types of recorders to various photometric detectors regardless of their peculiar input/output specifications.

Referring to the electrical diagram shown in FIG. 2, the electronic interface module comprises a quad or 4 element high-performance operational amplifier, of amplifier elements 40 through 46, preferably Part No. MC4741CP available from Motorola Corp., and operated by a power supply (not shown, preferably an Acopian D-15-15A). Amplifier 40 is connected through electrical lead 48 to the detector output terminal. The outputted signal originating in the detector is transmitted through amplifier 40 without amplification and with impedance buffering to avoid overloading of the detector output circuit.

A potentiometer 50 operated in a voltage divider mode is used to select a biasing reference voltage of between 0 and $-5$ V DC, which is transmitted to amplifier 42 operating in the same mode as amplifier 40.

The outputted positive voltage signal of amplifier 40 and the negative voltage signal of amplifier 42 are combined at junction 52 to produce a voltage that equals one-half the sum of the combined amplifier outputs. Resistors 54, 56 provide current limiting functionality in accordance with standard practice.

The combined signal is ultimately transmitted through a low pass filter comprised of resistor 58 and capacitor 60 to remove high frequency noise. The treated signal is inputted to amplifier 44 which is again arranged in a non-inverting mode, whereby the inputted signal from amplifiers 40, 42 is doubled through the selection of equally rated resistors 62, 64. Thus, the resulting effect is to produce an outputted signal from amplifier 44 which reduces, without net amplification, the detector output on a suppressed or reduced base line level, i.e., the detector output is compensated for without affecting small order base line disturbances, and may then be fed directly to a conventionally designed strip chart recorder, e.g., through lead 66.

The remaining element or amplifier 46 may be optionally employed to receive output from amplifier 44 and convert this signal to a form whereby the same may be used to operate signal processors which require relatively high input voltage levels, e.g., an integrator, microcomputer, etc. To this end, the inputted signal to amplifier 46 is processed in a non-inverting mode that yeilds an amplification factor of 100 through the selection of the ratio of resistors 68, 70. A capacitor 72 is additionally set in the circuit to remove high frequency output components in the signal. The amplified signal is ultimately received and used in an optional integrator or a like device through line connector or amplifier outlead 74.

OPERATION

Figure 5:
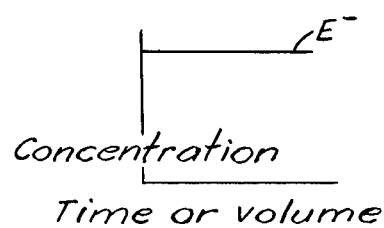
FIGS. 5 and 6 are generally representative of the appearance of photometrically derived chromatograms developed using the method of the analysis of the invention and are associated with the description of FIGS. 3 and 4.

For the purposes of illustrating anion analysis, FIG. 3 is a depiction of an anion exchange medium (stationary phase) in the operating condition of being pumped and equilibrated with mobile phase or liquid eluent comprising $C^+$ $E^-$ electrolyte, where $C^+$ is generically the co-ion to light-absorbing displacing eluent anions $E^-$. At the conclusion of the equilibration, the active ion exchange sites of the ion exchange medium are theoretically occupied exclusively by light-absorbing eluent anions $E^-$. A concentration monitor capable of sensing all ionic species and placed at the outlet of the ion exchange column would thus reveal a steady level of $C^+$ and $E^-$ if the feed concentration of the eluent is maintained constant (the photometrically derived chromatogram representation of FIG. 5).

Figure 4:
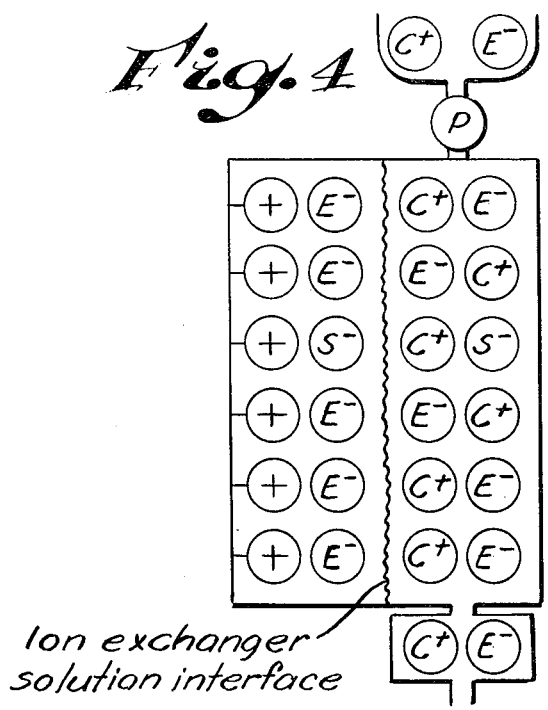

Assuming the subsequent injection of sample electrolyte denoted $C^+$ $S^-$ (FIG. 4), the sample anion $S^-$ is chromatographically retarded by attraction to the active ion exchange sites of the stationary phase and will exit in the ion exchange effluent at a characteristic elution volume determined by such factors generally as the capacity of the exchange medium, the concentration of the eluent and the affinity of the ion exchange sites or stationary phase for $S^-$ relative to $E^-$. These factors are well known and described, e.g., in U.S. Pat. No. 3,920,397; also by Small et al. "Proceedings of an International Conference on the Theory and Practice of Ion Exchange", University of Cambridge, U.K., July, 1976; and also by F. Helfferich, "Ion-Exchange", McGraw-Hill, 1962; (all incorporated herein by reference).

Figure 6:
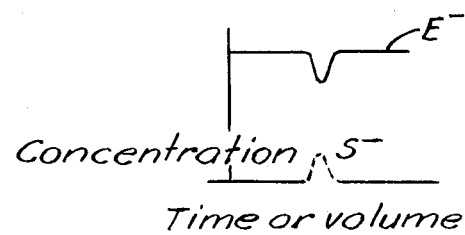

The invention is based on the principle that accompanying the appearance of $S^-$ sample ions in the effluent, there must be a concerted and equivalent change in the concentration of $E^-$ light absorbing displacing ions. This relationship is predetermined by the principles of electroneutrality and equivalence of exchange which require that the total equivalent concentrations of anions ($S^-$ and $E^-$) must remain fixed since the concentration of co-ions $C^+$ is fixed. Consequently, by monitoring effluent absorbance under conditions which permit the light-absorbing displacing ions to be photometrically distinguished from the sample, fluctuations are produced in the effluent absorbance signal as the concentration of the monitored displacing ions periodically gives way to eluting sample ions in the effluent. In the case of transparent sample ions, or sample ions of lesser absorbance than the displacing ions, a characteristic dip is accordingly observed in the effluent absorbance (the illustrative chromatogram of FIG. 6) from which an accurate determination of sample anion concentration can be made. Cation analysis is essentially identical in principle using as the stationary phase a suitable and equilibrated cation ion exchange medium, and as the mobile phase, $C^-$ electrolyte supplying light-absorbing cations as the displacing ions.

FURTHER PARAMETERS

The sensitivity of detection will be determined in larger part by how the trough depth (or peak height) compares to base line noise. Hence, the larger the fractional disturbance in base line caused by the sample, the greater the precision. Mathematical analysis generally shows that other considerations aside, the precision in determining trough depth, and hence the sensitivity of detection, will be improved the lower the concentration of eluent employed. However, there is a practical limit to how low a concentration of eluent ion may be used since too low a concentration of eluent will impose long run times and loss of sensitivity due to band spreading. Ideally, the run time should be no longer than the time necessary for adequate resolution of the peaks.

Sample concentration also predetermines the strength of the eluent concentration. Basically, the source of this limitation resides in the inability of the eluent to satisfactorily displace sample ion at a higher concentration than the displacing ions of the eluent. Using relatively small dilute samples, ($10^{-1}$ to $10^{-6}$ molar) experience has generally established that most workable displacing ion concentration in the eluent will be in the range of about $10^{-1}$ to $10^{-6}$ molar.

Since the elution of sample ions is revealed by monitoring the absorbance level of the eluent, the optical absorbance of the eluent (in the effluent) must also be sufficiently greater than noise to insure sensitive detection of the eluted species. This in turn calls for the use of light-absorbing displacing ions of high molar extinction coefficients since diluent eluent solutions are ordinarly used in typical analysis. From general experience, a desirable level of optical density is in the range of about 0.01 to 3, and more preferably, about 0.5 to 1.5 absorbance units at the monitored wavelength(s) or wavelength band.

Preferred eluents are thus selected on the combined basis of capability to elute sample ions within practical times, and adequate optical density.

Both the monitor and displacing functions can be found in ions with aromaticity. The aromaticity leads to high molar extinction coefficients in the U.V. and confers on the ions a relatively high affinity for the ion exchange separating mediums commonly used. For anion separations, specifically phthalate, trimesate (1,3,5 benzene tricarboxylate), toluene sulfonate, and benzene disulfonate are preferred for use as light-absorbing displacing ions—the phthalate especially so. With respect to the trimesate at pH 10, an exceptional sensitivity is observed relative to temperature changes in the column. Where such is manifested, the column is desirably encased in thermostated jacket, e.g., a circulating water jacket, maintained at constant temperature.

For cation separations, suitable eluents may be prepared using electrolyte solutions of pyridinium halides such as pyridinium chloride and bipyridinium dissociable compounds such as 4,4'-bipyridinium dihydrochloride (preferred for divalent cation separations) as the light-absorbing cation. Divalent copper such as from copper sulfate and aromatic quaternary ammonium ions such as obtained from the dissolution of benzyl trimethyl ammonium bromide are also disclosed for cation separations and indirect photometric detection.

Anion separations may also be performed using a non-light-absorber such as thiocyanate ion to which may be added, such as by constant flow addition to the ion exchange effluent, ferric ion to produce a visible species for photometric monitoring purposes. Similarly, protonated polyamine ions, such as ethylene diamine or diethylene amine may be used for cation separations and complexed with divalent copper ion under controlled pH conditions for photometric detection. Alternatively, and as an illustrative example only, divalent copper may be used for cation separations, and complexed with a polyamine additive for enhanced photometric detectability.

In addition to the displacing electrolyte, the eluent solution may also require buffer ions added to control either the valence of the monitor-displacing ion or the sample ions or both. The monitor-displacing ion may occasionally act as its own buffer. In addition, the displacing electrolyte may incorporate a major or minor portion of non-light-absorbing ions added for displacing functionality but which lack monitoring properties. The eluting power of the eluent may thus be derived solely from the monitor displacing ion or shared between the monitored ion and other ions in the system.

Ion exchange separating media used with the described eluent systems are preferably for anion separations, the low specific capacity, surface agglomerated form of anion exchange resin, e.g., described in U.S. Pat. Nos. 4,101,460 and 4,119,580, incorporated fully herein by reference.

Either a surface agglomerated form of low specific capacity cation exchange resin, e.g., prepared under the teaching of the above-identified patents, or low specific capacity surface sulfonated cation exchange resin beads in a non-agglomerated form, e.g., described in U.S. Pat. No. 3,966,596 (also fully incorporated by reference) can be suitably employed for cation separations.

The preferred separating media and eluent parameters are most suited to typical case analysis of dilute relatively small samples, in turn, beneficially calling for dilute eluent electrolytes and low specific capacity forms of separating media. Directly injected more concentrated or larger samples can be analyzed according to the method of the invention using corresponding stronger eluents and higher capacity separating media, as required in accordance with the principles of ion exchange chromatography. In any practice of the method of the invention, the optical density of the monitored ion is adjusted, e.g., by wavelength selection, to achieve a desirable optical density level to insure sensitive detection.

EXAMPLE 1

Two 2.8 × 250 mm Altex glass columns packed with a surface agglomerated resin form of separating medium are prepared according to the method of U.S. Pat. No. 4,119,580, using as the substrate, 8 percent cross-linked styrene divinyl benzene strong acid cation exchange resin (BioRad ® AG-50WX8, 37-44 μm Na+ form resin); and as the anion exchange latex deposit, a latex prepared by contacting polyvinyl benzyl chloride latex resin, containing about 5 weight percent divinylbenzene cross-linking agent, with excess dimethylethanolamine to form latex particles with active anion exchange sites. The latex is characterized as having a volume average diameter of about 0.6 micron.

The packed columns are connected in series and pumped, at 2 mls/min, with an Altex Model 110A pump. The eluent is $10^{-3}$ M disodium ortho-phthalate (pH = 7.8).

A Rheodyne 7010 sample injection valve with a 20 μl sample loop, is used to inject sample to the head of the columns whose exit is coupled to a LDC Model 1203 U.V. detector operating at 254 nm.

The output stage of the detector is connected to the above-described electronic suppressor 32, which impresses a potential counter to that developed by the detector. The resulting suppressed output is applied to a Linear ® Model 156 strip chart recorder.

The columns are pumped with eluent until the effluent absorbance is stable and equal to that of the eluent (1.124 absorbance units). The sensitivity of the detector is then set at 0.064 absorbance units full scale (A.U.F.S.) and the background suppressor circuit of the detector is adjusted so that the base line response on the recorder (set at 10 mv full scale) reads about 90-100 percent of full scale.

Figure 7:
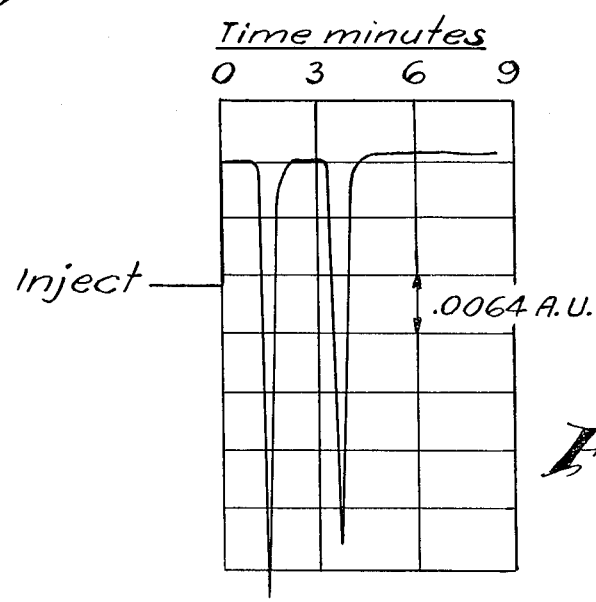

A sample solution of $10^{-3}$ M sodium chloride is injected and the recorder solid line trace of FIG. 7 is obtained-trough 1 being a disturbance at the void volume of the column while trough 2 at approximately 7.4 mls is due to elution of the chloride ion.

Further elutions of solutions of other anions give troughs at the following volumes of effluent:

| | |
|---|---|
| Bromide | 25.8 mls |
| Nitrate | 29.4 mls |
| Sulfate | 43.2 mls |
| Phosphate | 7.05 mls |
| Carbonate | 3.3 mls |
| Nitrite | 9.6 mls |
| Chlorate | 30.3 mls |
| Monochloro Acetate | 3.9 mls |
| Dichloro Acetate | 10.5 mls |
| Trichloro Acetate | 57.0 mls |

This Example serves to illustrate two important features of the invention:
(1) that ions may be resolved; and
(2) that they are detectable in the column effluent.

EXAMPLE 2

Separation of Ions

The columns of Example 1 are pumped at 2 mls/min with an eluent of slightly different composition $-10^{-3}$ M disodium ortho-phthalate $+10^{-3}$ M boric acid adjusted to pH 9 with sodium hydroxide.

Figure 10:
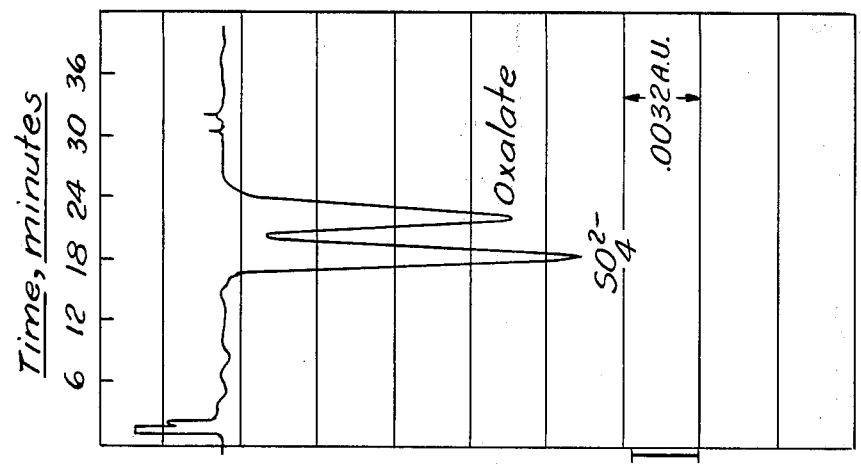
Figure 9:
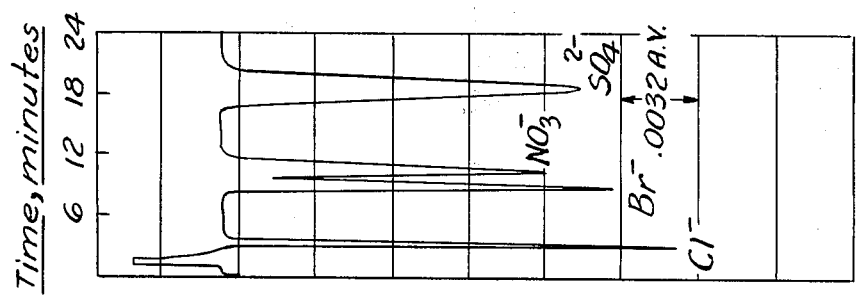
Figure 8:
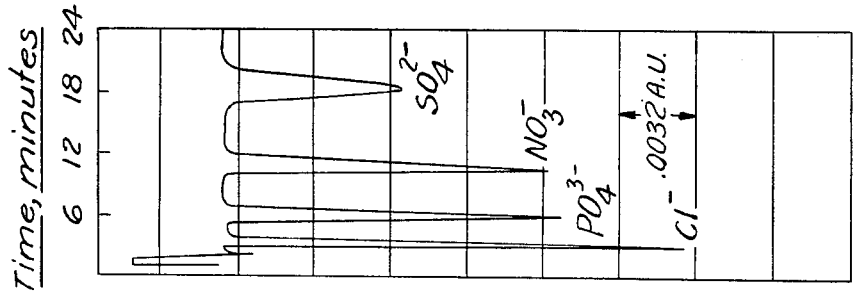

Injections of the following mixtures are made and the chromatograms of FIGS. 8 through 10 are obtained.

| | | |
|---|---|---|
| Sample Mixture A | 2 × $10^{-3}$ N Chloride<br>5 × $10^{-3}$ N Phosphate<br>5 × $10^{-3}$ N Nitrate<br>5 × $10^{-3}$ N Sulfate | Chromatogram FIG. 8 |
| Sample Mixture B | 2 × $10^{-3}$ M Chloride<br>5 × $10^{-3}$ M Bromide<br>5 × $10^{-3}$ M Nitrate<br>5 × $10^{-3}$ M Sulfate | Chromatogram FIG. 9 |
| Sample Mixture C | 5 × $10^{-3}$ M Sulfate<br>5 × $10^{-3}$ M Oxalate | Chromatogram FIG. 10 |

EXAMPLE 3

Calibration

The columns of Example 1 are pumped at 2 mls/min with $10^{-3}$ disodium ortho-phthalate $+10^{-3}$ boric acid adjusted to pH 8. The effluent absorbance when the columns reach equilibrium is 1.083 A.U. Various mixtures of nitrate, sulfate and phosphate are injected (20 $\mu$l injections) and the depths of their resulting troughs are measured. The sensitivity (A.U.F.S.) of the detector and the background suppressor are adjusted so as to keep the troughs on scale. The results are as follows:

TABLE I

| Sample Composition | Sensitivity (A.U.F.S.) | Trough Depth (cm) | | | Trough Depth Corrected for Sensitivity | | |
|---|---|---|---|---|---|---|---|
| | | $PO_4^{3-}$ | $NO_3^-$ | $SO_4^{2-}$ | $PO_4^{3-}$ | $NO_3^-$ | $SO_4^{2-}$ |
| $5 \times 10^{-3}$ N $PO_4^{-3}$, $NO_3^-$, $SO_4^{2-}$ | .032 | 12.6 | 11 | 5.9 | 12.6 | 11 | 5.9 |
| $2.5 \times 10^{-3}$ N $PO_4^{-3}$, $NO_3^-$, $SO_4^{2-}$ | .032 | 6.4 | 5.45 | 3.0 | 6.4 | 5.45 | 3.0 |
| $10^{-3}$ N $PO_4^{-3}$, $NO_3^-$, $SO_4^{2-}$ | .016 | 4.85 | 4.4 | 2.36 | 2.42 | 2.2 | 1.18 |
| $10^{-3}$ N $PO_4^{-3}$, $NO_3^-$, $SO_4^{2-}$ | .008 | 9.8 | 8.8 | 4.9 | 2.45 | 2.2 | 1.22 |

Figure 11:
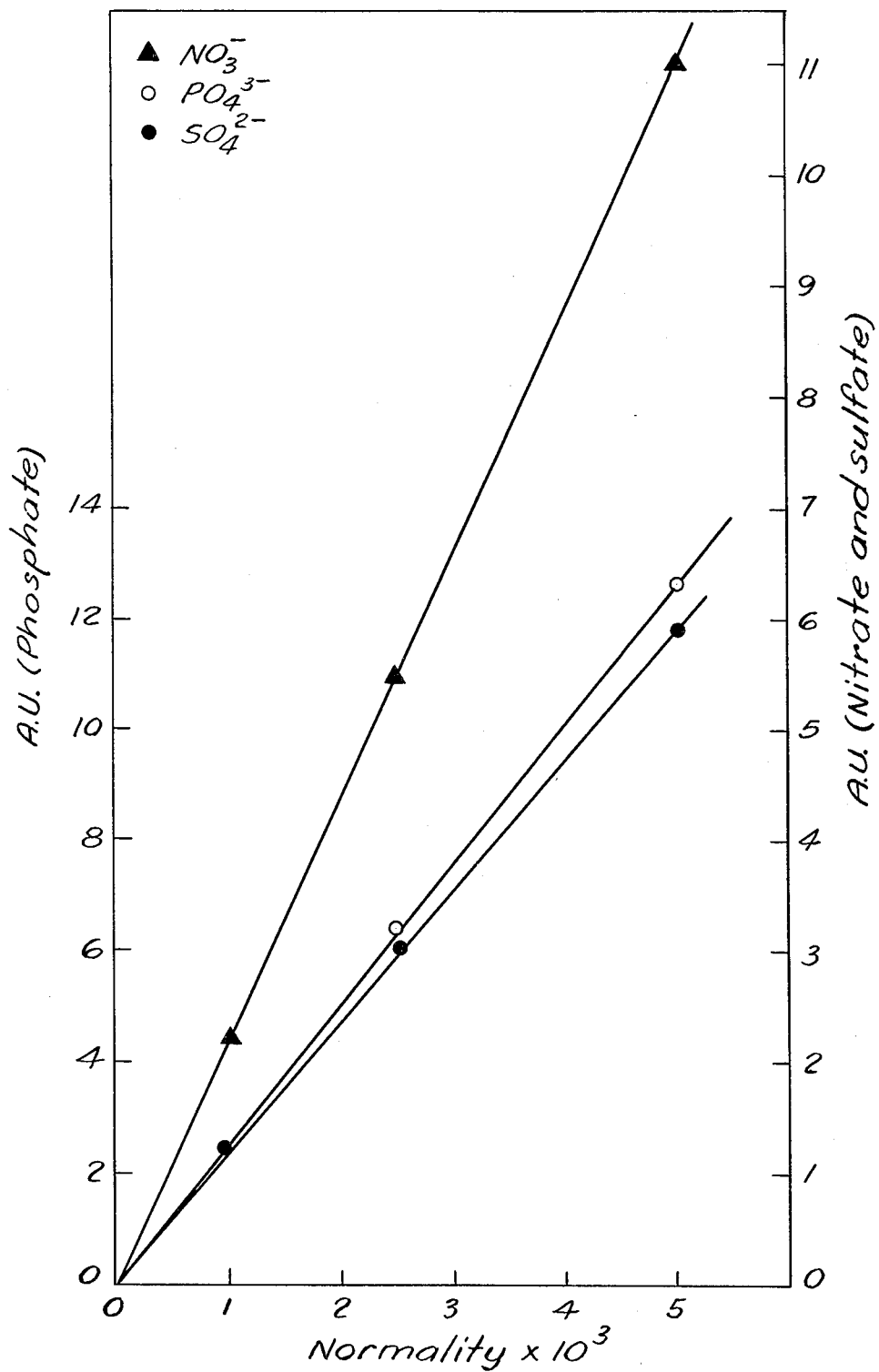

Calibration curves for the three ions are shown in FIG. 11 where it can be seen that at least over this limited range of concentration there is a close to linear dependence of trough depth to the amount of ion injected.

EXAMPLE 4

Common Response Factors

The experimental conditions of Example 3 are used in this example and separate injections made of sodium nitrate, sodium sulfate and sodium phosphate.

The purpose of this experiment is to establish how trough area depends on the ion injected. Lacking a suitable operating integrator, trough area is approximated by measuring the weight of chart paper contained in the troughs.

TABLE 2

| | Results: | |
|---|---|---|
| | Wt. of Trough (mgm) Corrected for Chart Speed | Wt. of Trough/ meq/l of Ion Injected |
| $5 \times 10^{-3}$ M Sodium Nitrate | 117.5 | 23.5 |
| $2.5 \times 10^{-3}$ M Sodium Sulfate | 110.8 | 22.2 |
| $1.67 \times 10^{-3}$ M Sodium Phosphate | 80.4 | 24.1 |

The area of the trough/equivalent of ion is approximately independent of the ion injected for these three ions. On the basis of this observation, it would be expected that anions of strong acids (pK $<4$) would as a general matter adhere to this rule. Anions of acids with medium to high pK's should give responses determined by their valence at the ambient pH of the eluent. Phosphate, for example, exists predominantly as the $HPO_4^{-2}$ species at pH 8 so that one mole of phosphate injected would be expected to displace two equivalents of monitor ion. The data of Table 2 supports this expectation.

EXAMPLE 5

Different Monitor Ions (A) A single column prepared in the manner of Example 1 is pumped at 2 mls/min with a solution $2 \times 10^{-3}$ M sodium toluene sulfonate; $10^{-3}$ M boric acid adjusted to pH 8. The toluene sulfonate ion is the monitor ion and the major displacing ion. Samples containing various anions are injected and elution volumes determined as follows:

| Carbonate | 3.45 mls |
|---|---|
| Chloride | 7.8 mls |
| Nitrite | 10.5 mls |
| Chlorate | 31.8 mls |
| Phosphate | 58.8 mls |
| Monochloro Acetate | 4.05 mls |
| Dichloro Acetate | 11.6 mls |

(B) A single column prepared in the manner of Example 1 is pumped at 2 mls/min with eluents containing trimesate ion as displacing/monitor ion. Elution volumes of various ions are determined as follows:

| | Elution Volumes (mls) | |
|---|---|---|
| Anion Injected | in Trimesate Eluent X* | in Trimesate Eluent Y* |
| Chloride | 1.57 | 1.37 |
| Sulfate | 2.18 | 1.75 |
| Iodide | 23.1 | 9.7 |
| Thiocyanate | 17.4 | 14 |
| Perchlorate | >30 | 32 |
| Dichloro Acetate | 1.65 | 1.55 |
| Trichloro Acetate | 3.65 | 3.06 |
| Citrate | 7.2 | 4.52 |
| Pyrophosphate | 8.4 | 5.6 |

*X = $2.5 \times 10^{-4}$ M trisodium trimesate; $10^{-3}$ M boric acid - pH = 7.2
*Y = $5 \times 10^{-4}$ M trisodium trimesate; $10^{-3}$ M boric acid - pH = 7.4

This example illustrates how more tightly held ions such as thiocyanate, perchlorate and citrate may be effectively displaced by a more potent displacing ion such as the trimesate ion which is also the monitor ion.

In Ion Chromatography, these more tightly held ions are usually displaced in conveniently short times by increasing the concentration of the eluent. This can greatly reduce the interval between successive suppressor exhaustions which is an inconvenience. The invention does not suffer from that drawback.

EXAMPLE 6

Reference Cell Suppression

Figure 12:
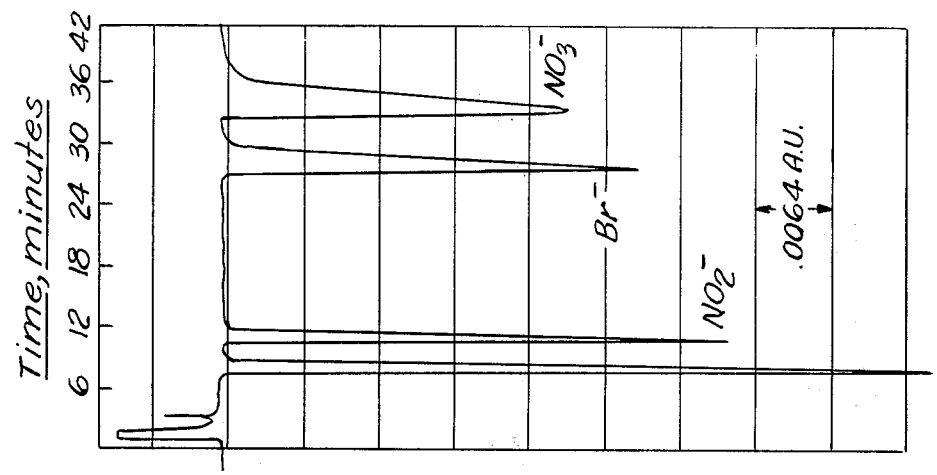

A sample of $10^{-3}$ molar of each of sodium nitrite and sodium chloride and $2 \times 10^{-3}$ molar of each of sodium bromide and sodium nitrate is injected onto a $4.1 \times 250$ mm stainless steel column packed with a surface agglomerated form of anion exchange resin as described in Example 1, except substituting as the substrate, Dowex ® $50 \times 8$ 20 $\mu$m, Na$^+$ form cation exchange resin. Eluent of $10^{-3}$ molar disodium ortho-phthalate $+10^{-3}$ molar boric acid, adjusted to pH 8, is pumped at a rate of 2 ml/min to the column, and by way of a stream splitter T-fitting, is simultaneously pumped at a rate of about 1.25 ml/min to the reference cell of an LDC 1203 photometer set at 254 nm. An illustration of the resulting chromatogram is shown as FIG. 12.

This alternative use of reference cell suppression (to electronic suppression), can be beneficial when alternating the sensitivity of the photometric detector between or during analysis runs. Reference cell suppression also beneficially adjusts for drifts in base line absorbance caused by eluent factors, and would be desirably used, e.g., when returning spent eluent to the eluent reservoir for recycling.

EXAMPLE 7

Further Anions

An Altex photometric detector, Model 153, set at 254 nm and operating with reference cell suppression using a Sage pump Model 355 to feed eluent directly from the eluent reservoir to the reference cell of the detector, is used under the following varied "Conditions" A through F for anion analysis.

Common conditions are column size, 4.1×250 mm; eluent pumping rate, 2 ml/min; and resin type (the Example 7 agglomerated anion form resin). The resin type is varied, however, in the volume average diameter (VAD) of the latex particles attached to a common form substrate (Dowex ® 50×8), as detailed below:

| Condition | Latex VAD | Eluent |
|---|---|---|
| A | 0.6 micron | $10^{-3}$ M Sodium trimesate; $10^{-3}$ M Boric Acid: pH = 9 |
| B | 0.6 micron | $5 \times 10^{-4}$ M Sodium trimesate: $10^{-3}$ M Boric acid: pH = 9 |
| C | 0.6 micron | $2.5 \times 10^{-4}$ M Sodium trimesate; $10^{-3}$ M Boric acid: pH = 9 |
| D | 0.6 micron | $10^{-3}$ M Disodium ortho-phthalate; $10^{-3}$ M Boric acid: pH = 9 |
| E | 0.4 micron | $10^{-3}$ M Disodium ortho-phthalate; $10^{-3}$ M Boric acid: pH = 9 |
| F | 0.09 micron | $10^{-3}$ M Disodium ortho-phthalate; $10^{-3}$ M Boric acid: pH = 9 |

Table 3 summarizes the results achieved, in terms of elution volumes of various tested anion species, using the eluent/separating medium Combinations A-F described above.

TABLE 3
ELUTION VOLUMES OF ANIONS

| Ion | Elution Volumes (mls) | | | | | |
|---|---|---|---|---|---|---|
| | A | B | C | D | E | F |
| Void | 2.2 | 2.0 | 2.1 | 2.0 | 2.4 | 2.1 |
| Acetate | e.i.v. | — | — | 3.2 | 3.4 | e.i.v. |
| Azide | 7.2 | — | — | 55 | 25 | 6.1 |
| Bromate | 3.4 | — | — | 14 | 8.75 | 3.15 |
| Bromide | 9 | 10.4 | 10.3 | 69 | 30 | 7.3 |
| Carbonate | 2.7 | 2.6 | 2.95 | 6.5 | 5.3 | 2.5 |
| Chlorate | 8.8 | 10.2 | 12.1 | 86 | 35 | 8.25 |
| Chloride | 3.9 | 4.20 | 4.95 | 17.1 | 10.3 | 3.4 |
| Mono-Chloroacetate | 2.75 | 2.76 | 3.16 | 8.0 | 6.2 | 2.6 |
| Di-Chloroacetate | 4.6 | — | — | 27.5 | 15.6 | 4.4 |
| Tri-Chloroacetate | 14.6 | 16.5 | 20 | t | t | 15.0 |
| Citrate | 14.7 | 26.8 | 52 | t | t | t |
| Cyanate | — | — | — | 6.5 | 5.25 | 2.3 |
| Dithionate | 5.3 | — | — | — | — | 14.0 |
| Fluoride | e.i.v. | — | e.i.v. | 3.0 | 3.2 | e.i.v. |
| Fumarate | — | — | — | — | 91 | 17.3 |
| Glycolate | e.i.v. | — | — | 3.4 | 3.45 | e.i.v. |
| Iodate | e.i.v. | — | — | 3.8 | 3.8 | e.i.v. |
| Iodide | 55 | — | — | — | — | 45 |
| Maleate | 4.0 | — | — | 78 | 53 | 11 |
| Malonate | 3.8 | — | — | 62 | 44 | 9.4 |
| Nitrate | 9.1 | — | 12.6 | 84 | 34 | 8.2 |
| Nitrite | 4.5 | — | — | 24.1 | 17.0 | 4.0 |
| Oxalate | 5.75 | — | — | — | — | 16.0 |

TABLE 3-continued
ELUTION VOLUMES OF ANIONS

| Ion | Elution Volumes (mls) | | | | | |
|---|---|---|---|---|---|---|
| | A | B | C | D | E | F |
| Perchlorate | t | — | — | — | — | t |
| Persulfate | 4.8 | — | — | — | 68 | 13.4 |
| o-Phosphate | 3.1 | — | — | 7.5 | 24.6 | 6.3 |
| Propionate | e.i.v. | — | — | 3.3 | 3.4 | e.i.v. |
| Pyrophosphate | 51 | — | — | — | — | — |
| Succinate | 3.3 | — | — | 47 | 36 | 7.9 |
| Sulfate | 5.0 | 6.45 | 9.4 | 114 | 67 | 14 |
| Sulfite | — | — | — | 86 | — | — |
| Tartarate | 4.9 | — | — | — | — | — |
| Thiocyanate | 86 | — | — | — | — | t | e.i.v. = Eluted in void trough.
t = Very large; experiment terminated before species eluted.

EXAMPLE 8

Separation and Detection of Cations

This experiment illustrates the separation and detection of mixed sodium and calcium ions, using as the eluent, an aqueous solution of $5 \times 10^{-3}$ M pyridine adjusted to pH 4.5 by the addition of HCl. Weakly basic pyridine is thus converted to cationic pyridinium ion (pKa 5.25) with the dual role of displacing ion in the separating column and monitor ion in the UV detector.

The chromatographic column is a commercially available Whatman Partisil-10 SCX s.s. column of 250 mm length and 4.6 mm I.D. Its 10 micron particle packing is a silica gel with siloxane-bonded sulfonic acid functional groups.

A Constametric I LDC pump is used to pump the eluent at 2 mls/min (2,350 psig) consecutively through a Rheodyne 7010-A sample valve (20 microliter injection), Partisil-SCX column and Perkin-Elmer Model 75 HPLC/UV detector set for 265 nm analysis wavelength.

This chromatographic combination produces baseline resolution of sodium and calcium, with the sodium trough appearing at 10 mls, and the calcium trough at 18 mls (see FIG. 13). Separation of monovalent ions would be expected to improve with high performance surface latex agglomerated resins, e.g., described in U.S. Pat. Nos. 4,101,460 and 4,119,580.

EXAMPLE 9

Eluent Effects on the Detection Limits

This Example is used to illustrate the effect various eluents have on detection limits of a given sample standard of mixed alkali metal cations. The experiment uses as the separating medium, a low specific capacity cation exchange resin prepared by the surface sulfonation of 2 percent cross-linked sytrene divinyl benzene copolymer resin, 180–400 U.S. standard mesh size, using 5 minutes reaction time of preheated (93° C.) resin in preheated (93° C.) concentrated sulfuric acid, followed by rapid quenching in deionized water (the method of U.S. Pat. No. 3,966,596).

The experiment uses the following common conditions:

| Eluent flow rate: | 2 ml/min | |
|---|---|---|
| Column: | 9 × 235 mm | |
| | Wt % | Molarity |
| Sample: 20 µl | 425 ppm LiCl | $10^{-2}$ |
| | 585 ppm NaCl | $10^{-2}$ |

-continued

| | | |
|---|---|---|
| 745 ppm KCl | $10^{-2}$ |
| 745 ppm KCl | $10^{-2}$ |
| 1210 ppm RbCl | $10^{-2}$ |
| 1685 ppm CsBr | $10^{-2}$ |

Table 4 below defines the variable conditions of the experiment also giving the calculated detection limit for each resolved cation species using the criterion of a signal/noise ratio of 2. In addition, the resulting chromatogram, using the preferred pyridinium chloride eluent is reproduced in the drawing as FIG. 14 and illustrates the favorable separation of the $K^+$, $Rb^+$ and $Cs^+$ ion species from $Na^+$ and $Li^+$.

TABLE 4

| Eluent and Molarity | $2.5 \times 10^{-3}$ M benzyltrimethyl ammonium bromide | $10^{-3}$ M copper sulfate | $5 \times 10^{-3}$ M pyridinium chloride |
|---|---|---|---|
| Analysis Wavelength and Baseline Absorbance | 260 nm 0.70 A.U. | 275 nm 0.46 A.U. | 267 nm 1.00 A.U. |
| Detection Limit (ppm) | | | |
| $Li^+$ | —(1) | —(1) | —(1) |
| $Na^+$ | 3.4 | —(1) | —(1) |
| $K^+$ | —(1) | 146 | 16.2 |
| $Rb^+$ | 12.4 | 321 | 35.6 |
| $Cs^+$ | 15.4 | 395 | 43.8 |

(1) co-eluting species

EXAMPLE 10

Separation and Detection of Divalent Cations

This experiment illustrates the separation and detection of tightly bound divalent cations using an eluent of high displacing power, comprising a solution of $5 \times 10^{-3}$ M 4,4'-bipyridinium dihydrochloride in deionized water. Two samples are analyzed, specifically, a sample of $10^{-2}$ M of each of copper chloride, magnesium chloride and calcium chloride; and a sample of $10^{-2}$ M of each of cobaltous chloride and calcium chloride. The analysis wavelength is set at 307.2 nm using the further conditions of analysis described with respect to Example 9. Base line separation and detection of all divalent ion species is achieved. Reproductions of the chromatograms are shown in the drawing as FIGS. 15 and 16. The cause for an observed disturbance "A" between the $Cu^{++}$ and $Mg^{++}$ troughs of the FIG. 15 chromatogram is not yet explained.

EXAMPLE 11

Signal Optimization

This experiment is to vary only the analysis wavelength, and thus the base line absorbance, and observe the effect on the detection limit. The detection limit is defined as that concentration of sample giving a trough depth only twice as large as the noise or a signal-to-noise ratio of 2. "Detection limit" is equivalent to "sensitivity". Conditions of the experiment are as follows:

Eluent: $5 \times 10^{-3}$ M pyridinium chloride, buffered to pH 4.5 using HCl
Flow Rate: 2 cc/min
Column: Partisil-10 SCX from Whatman (#IE 3586) 250×4.6 mm, microparticulate 10 micron silica gel packing with sulfonic acid functional groups. (2,350 psig at 2 cc/min, 23° C.) 3 cc total column volume has 0.180 meq capacity.
Sample: 20 μl of 250 ppm NaCl, 1000 ppm $CaCl_2$
Detector: Perkin-Elmer LC-75 variable wavelength single beam visible/UV detector for liquid chromatography; 8 microliter, 6 mm cell.

The analysis wavelength is varied as shown in the Table 5 of the recorded data below. Absorbance values are in relation to zero absorbance defined at 280 nm wavelength reference.

TABLE 5

| | λ (Å) | Pyridinium Absorbance (A.U.) | Signal $Ca^{++}$ Trough Depth (A.U. × $10^{-4}$) | Noise Trough to Trough (A.U. × $10^{-4}$) | Sensitivity $\frac{1000 \text{ ppm}}{S/N} \times 2$ (ppm) |
|---|---|---|---|---|---|
| 1. | 2721 | 0.128 | 14 | 3 | 155 |
| 2. | 2693 | 0.256 | 61 | 3 | 35.5 |
| 3. | 2670 | 0.512 | 156 | 3 | 13.9 |
| 4. | 2654 | 0.768 | 246 | 4 | 11.7 |
| 5. | 2644 | 1.024 | 306 | 5 | 11.8 |
| 6. | 2637 | 1.280 | 342 | 6 | 12.4 |
| 7. | 2631 | 1.536 | 360 | 8 | 15.6 |
| 8. | 2625 | 1.792 | 360 | 11 | 22.0 |
| 9. | 2619 | 2.048 | 308 | 14 | 32.8 |
| 10. | 2612 | 2.304 | 188 | 17 | 65.2 |
| 11. | 2606 | 2.560 | 24 | 20 | 601 |

The experiment of Example 11 illustrates that sensitivity optimization is obtained by balancing the competing effects of noise, which increases with increasing base line absorbance; and in this case trough depth, which to an optimum value increases with base line absorbance increases, and thereafter diminishes. It also shows that over an absorbance range of about 0.5 to 1.5 absorbance units, sensitivity performance is essentially equivalently good.

What is claimed is:

1. A single column method of ion analysis using sensitive photometric detection in which liquid eluent containing monitor/displacing ions is added with sample to an ion exchange liquid chromatography column under suitable conditions to resolve for detection purposes sample ions of interest which elute as sample bands in the effluent of the column, the sample ions being of the same charge and less absorbing than the monitor/displacing ions at the chosen photometric monitoring conditions in order to indirectly measure sample bands of interest by the decrements they cause in the absorbance response of the eluent, said method being characterized by the selection and use of an eluent which contains not greater than about $5 \times 10^{-3}$ molar of said monitor/displacing ions for the purpose of sensitive detection by the photometric monitoring step of the indirectly detected sample ions of interest.

2. The method as in claim 1 further characterized by using as the monitor/displacing ions, aromatic organic ions.

3. The method as in claim 1 in which polyvalent aromatic organic ions are used as the monitor/displacing ions.

4. The method as in any one of the preceding claims, in which an eluent is selected and used for sensitive photometric detection of the indirectly detected sample ions of interest using not greater than about $5 \times 10^{-4}$ molar of said monitor/displacing ions.

5. The method as in claim 1 for anion analysis in which a phthalate, trimesate, a toluene sulfonate, or a benzene disulfonate anion serves as the monitor/displacing ions of the eluent.

6. The method as in claim 1 for cation analysis in which a pyridinium, a bipyridinium, divalent copper, or an aromatic quaternary ammonium cation serves as the monitor/displacing ions of the eluent.

7. The method as in claim 1 using the step of adding a reagent to the column effluent to produce light-absorbing monitor/displacing ions suitable for the purposes of the photometric monitoring step.

8. A liquid chromatographic method for the photometric determination of transparent sample ions comprising the steps of passing a liquid eluent containing monitor/displacing ions of the same charge as the sample ions of interest through an ion exchange stationary phase, introducing sample into the stream of eluent, passing the combined eluent and sample through said ion exchange stationary phase effecting sequential chromatographic displacement of the sample ions into the effluent of the ion exchange stationary phase and under conditions whereby sample ions of interest elute as sample bands sufficiently resolved for detection purposes, photometrically monitoring said effluent using light which is detectably absorbed by the monitor/displacing ions at a level greater than the sample ions, and indirectly determining the concentration of displaced sample ions of interest eluting from the ion exchange stationary phase based on the decrements in effluent absorbance caused by the less absorbing transparent sample ions, the improvement which comprises using as the monitor/displacing ions, aromatic organic ions.

9. The method as in claim 8 further characterized by the selection and use of an eluent which contains not greater than about $5 \times 10^{-3}$ molar of said monitor/displacing ions.

10. The method as in claim 8 or 9 for anion analysis in which a phthalate, trimesate, a toluene sulfonate, or a benzene disulfonate anion serves as the monitor/displacing ions of the eluent.

11. The method as in claim 8 or 9 for cation analysis in which a pyridinium, a bipyridinium, divalent copper, or an aromatic quaternary ammonium cation serves as the monitor/displacing ions of the eluent.

12. The method as in claim 11 in which polyvalent aromatic organic ions are used as monitor/displacing ions.

13. The method as in any one of the claims 11–13, in which an eluent is selected and used for sensitive photometric detection of the indirectly detected sample ions of interest using not greater than about $5 \times 10^{-4}$ molar of said monitor/displacing ions.

14. A liquid chromatographic method for the photometric determination of transparent sample ions comprising the steps of passing a liquid eluent containing monitor/displacing ions of the same charge as the sample ions of interest through an ion exchange stationary phase, introducing sample into the stream of eluent, passing the combined eluent and sample through said ion exchange stationary phase effecting sequential chromatographic displacement of the sample ions into the effluent of the ion exchange stationary phase and under conditions whereby sample ions of interest elute as sample bands sufficiently resolved for detection purposes, photometrically monitoring said effluent using light which is detectably absorbed by the monitor/displacing ions at a level substantially greater than the sample ions, and indirectly determining the concentration of displaced sample ions of interest eluting from the ion exchange stationary phase based on the decrements in effluent absorbance caused by the less absorbing transparent ions as measured by peak height, the improvement which comprises using as the monitor/displacing ions, ions which have high affinity for the stationary phase relative to the sample ions of interest to prevent loss of sensitivity due to band spreading of the eluted transparent sample bands, said monitor/displacing ions being used at a concentration of not greater than about $5 \times 10^{-3}$ molar for purposes of sensitive detection by the photometric monitoring step of the transparent sample ion bands.

15. The method as in claim 14 in which a polyvalent ion or a monovalent aromatic organic ion serves as the monitor/displacing ion.

16. The method as in claim 15 in which the monitor/displacing ions comprise polyvalent aromatic organic ions.

17. The method as in any one of the claims 14–16, in which an eluent is selected and used for sensitive photometric detection of the indirectly detected sample ions of interest using not greater than about $5 \times 10^{-4}$ molar of said monitor/displacing ions.

18. The method as in claim 14 for anion analysis in which a phthalate, trimesate, a toluene sulfonate, or a benzene disulfonate anion serves as the monitor/displacing ions of the eluent.

19. The method as in claim 14 for cation analysis in which a pyridinium, a bipyridinium, divalent copper, or an aromatic quaternary ammonium cation serves as the monitor/displacing ions of the eluent.

20. The method as in claim 14 using the step of adding a reagent to the column effluent to produce light-absorbing monitor/displacing ions suitable for the purposes of the photometric monitoring step.

* * * * *

UNITED STATES PATENT AND TRADEMARK OFFICE
CERTIFICATE OF CORRECTION

PATENT NO. : 4,414,842
DATED : November 15, 1983
INVENTOR(S) : Hamish Small et al.

It is certified that error appears in the above—identified patent and that said Letters Patent is hereby corrected as shown below:

Col. 1, line 21, delete "seperation" and insert --separation--.

Col. 3, line 6, delete "uniqiue" and insert --unique--.

Col. 7, line 12, delete "yeilds" and insert --yields--.

Col. 8, line 48, delete "monitor" and insert --monitoring--.

Col. 13, line 47, delete "Volumes" and insert --Volume--.

Col. 14, line 54, delete "sytrene" and insert --styrene--.

Col. 15, line 3, delete "745 ppm KCl $10^{-2}$", second instance.

Col. 17, Claim 12, line 42, delete "11" and insert --8--.

Col. 17, Claim 13, line 45, delete "11-13" and insert --8 or 12--.

Signed and Sealed this

Fifth Day of June 1984

[SEAL]

Attest:

Attesting Officer

GERALD J. MOSSINGHOFF

Commissioner of Patents and Trademarks